US008198897B2

(12) United States Patent
Ando et al.

(10) Patent No.: US 8,198,897 B2
(45) Date of Patent: Jun. 12, 2012

(54) SUPERCONDUCTIVE MAGNETIC DEVICE, MAGNETIC RESONANCE IMAGING APPARATUS AND MAGNETIC FIELD INHOMOGENEITY COMPENSATION METHOD

(75) Inventors: Ryuya Ando, Ibaraki (JP); Kenji Sakakibara, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 339 days.

(21) Appl. No.: 12/593,426

(22) PCT Filed: Apr. 10, 2008

(86) PCT No.: PCT/JP2008/057075
§ 371 (c)(1),
(2), (4) Date: Sep. 28, 2009

(87) PCT Pub. No.: WO2008/126895
PCT Pub. Date: Oct. 23, 2008

(65) Prior Publication Data
US 2010/0045293 A1 Feb. 25, 2010

(30) Foreign Application Priority Data

Apr. 10, 2007 (JP) ................................. 2007-102560

(51) Int. Cl.
*G01V 3/00* (2006.01)
(52) U.S. Cl. ....................................... 324/319; 324/315
(58) Field of Classification Search .......... 324/300–322; 600/407–445
See application file for complete search history.

(56) References Cited

U.S. PATENT DOCUMENTS

| | | | | |
|---|---|---|---|---|
| 6,252,405 B1 * | 6/2001 | Watkins et al. | ............... | 324/319 |
| 6,788,060 B1 * | 9/2004 | Feenan et al. | .................. | 324/320 |
| 6,825,667 B1 * | 11/2004 | Tsuda | ........................... | 324/320 |
| 7,071,694 B1 | 7/2006 | Kruip | | |
| 7,432,708 B2 * | 10/2008 | He et al. | ........................ | 324/315 |
| 7,741,847 B2 * | 6/2010 | Nakabayashi et al. | ........ | 324/320 |
| 2012/0041291 A1 * | 2/2012 | Ferren et al. | .................. | 600/365 |

FOREIGN PATENT DOCUMENTS

| | | | |
|---|---|---|---|
| GB | 2355800 A | | 5/2001 |
| JP | 08-215168 | * | 8/1996 |
| JP | 8-215168 | | 8/1996 |
| JP | 2004-351207 | | 12/2004 |
| JP | 2006-305146 | | 11/2006 |

\* cited by examiner

*Primary Examiner* — Brij Shrivastav
(74) *Attorney, Agent, or Firm* — Cooper & Dunham LLP

(57) ABSTRACT

The magnetic field homogeneity adjusting device (20) is characterized by comprising a magnetic field distribution measuring unit (21) for measuring the magnetic field distribution in the magnetic field space, a temperature variation calculating unit (22) for calculating the temperature variation of the ferromagnetic bodies needed to improve the homogeneity of the magnetic field space based on the measured magnetic field distribution, and a temperature control unit (12) for setting a temperature control value of the ferromagnetic bodies according to the calculated temperature variation.

16 Claims, 9 Drawing Sheets

SUPERCONDUCTIVE MAGNETIC DEVICE, MAGNETIC RESONANCE IMAGING APPARATUS AND MAGNETIC FIELD INHOMOGENEITY COMPENSATION METHOD

TECHNICAL FIELD

The present invention relates to a superconductive magnetic apparatus, magnetic resonance imaging apparatus and magnetic field inhomogeneity compensation method.

BACKGROUND ART

In the past, a magnetic resonance imaging apparatus for generating static magnetic field using a superconductive magnetic device has been widely used particularly in the field of clinical diagnosis. A magnetic resonance imaging apparatus is capable of acquiring images which exhibit physical and chemical properties of an object to be examined, using nuclear magnetic resonance phenomenon generated when high-frequency pulses are irradiated to the object (examinee) placed in a homogeneous static magnetic field space. A magnetic resonance imaging apparatus is configured mainly comprising a magnetic device as a magnetic field generating source for applying homogeneous static magnetic field in an imaging region into which the object is to be carried, an RF coil for irradiating high frequency pulses toward the imaging region, a reception coil for receiving response from the imaging region and a gradient magnetic field coil for applying a gradient magnetic field so as to provide positional information of resonance phenomena to the imaging region.

In magnetic resonance imaging apparatus, one of the requirements for improving image quality is improvement of static magnetic field homogeneity. Given this factor, upon designing and manufacturing of a magnetic device to be used for a magnetic resonance imaging apparatus, adjustment of magnetic field is carried out in the respective steps of designing, assembling and installation, in order to make uniform the static magnetic field generated in the imaging region by a magnetic field generating source.

As for the magnetic field adjustment in the installation step for the purpose of adjusting inhomogeneous components generated due to manufacturing errors or surrounding environment, it is often carried out by incrementally disposing or taking off a magnetic homogeneity adjusting body formed by a magnetic material to a magnetic device (for example, refer to Patent Document 1). This magnetic field homogeneity adjusting body is generally disposed in the space between the magnetic field generating source and a gradient magnetic field coil to be disposed inside thereof (imaging region side) using a magnetic field homogeneity adjusting mechanism (means), etc.

On the other hand, magnetic field homogeneity of a magnetic device varies on a long-term or short term basis due to environmental fluctuation such as air temperature. Here, even though it is possible to adjust magnetic field using the above-mentioned magnetic field homogeneity adjusting body in order to further correct fluctuation of magnetic field homogeneity, it is not appropriate to perform such adjustment of magnetic field homogeneity every time since it usually takes a long time for such adjustment operation. Given this factor, various methods have been developed for absorbing such fluctuation of magnetic field homogeneity.

One of them is the method to mount in advance a plurality of coils for adjusting a magnetic field in the magnetic device and/or a gradient magnetic field coil, calculate the current value for compensating fluctuation of magnetic field homogeneity, and energize the relevant coil. For example, in Patent Document 2, the technique is disclosed to measure the temperature of a magnetic material which configures the magnetic circuit of the magnetic device, calculate the applied current value of the coil for adjusting the magnetic field based on the measured temperature and distribute power to the coil based on the relevant applied current value, so as to obtain a homogeneous magnetic field.

On the contrary, the method for suppressing temperature fluctuation of the magnetic material itself has also been developed. For example, in Patent Document 3, the method is described for covering the static magnetic field generating source with heat insulating material, heating material and a heater so as to keep a constant temperature of the static magnetic field generating source by applying heat with the heater. Also in Patent Document 4, the method is described for disposing a cooling device in addition to heating so as to improve accuracy of temperature control by freely using the provided devices.

Further, the method has been developed for achieving magnetic field homogeneity by actively using distribution of magnetization intensity generated by temperature distribution of the magnetic material. For example, the method is described in Patent Document 5 for obtaining magnetic field homogeneity by adjusting temperature distribution of a permanent magnet, and the method for obtaining magnetic field homogeneity by adjusting temperature distribution of the entire magnetic device is described in Patent Document 6. Also, while the superconductive magnet comprising a pole piece is described in Patent Document 7, adjustment of temperature distribution of the pole piece is not described therein.

Patent Document 1: Japanese Patent No. 3733441
Patent Document 2: Japanese Patent No. 3781166
Patent Document 3: JP-B-H3-28931
Patent Document 4: JP-A-H3-109043
Patent Document 5: JP-A-2003-116807
Patent Document 6: Japanese Patent No. 3559364
Patent Document 7: Japanese Patent No. 3559364

DISCLOSURE OF THE INVENTION

Problems to be Solved

In the case of the superconductive magnet including at least one pair of ferromagnetic bodies in a part of the magnetic circuit, not only the temperature fluctuation of the above-mentioned magnetic material but also the applied current value of the superconductive coil becomes the fluctuation factor of magnetic field homogeneity. For example, in the case of demagnetizing or exciting the superconductive magnet due to periodic maintenance of the superconductive magnet, if the applied current value before demagnetization and the applied current value after re-excitation do not match, an inhomogeneous magnetic field will be generated which is equivalent to the error in the current value.

The above-described generation of inhomogeneous magnetic field distribution can be explained below using FIG. 9. In FIG. 9, the lateral axis indicates azimuthal angle (degrees) of the homogeneous magnetic field space, and the vertical axis indicates the magnetic field intensity in the direction thereof (excluding the homogeneous components). In the superconductive magnet of the method which obtains homogeneous magnetic field by placing at least one pair of superconductive coils and at least one pair of ferromagnetic bodies facing each other, homogeneous magnetic field J3 is formed by adding magnetic field distribution J1 produced by the superconductive coil and magnetic field distribution J2 produced by the ferromagnetic bodies.

Here, if the applied current value of the superconductive coil changes before demagnetization and after re-excitement, the superconductive coil generates magnetic field variation C1 in proportion to the current variation, and magnetic field distribution J1 produced by the superconductive coil turns to be magnetic field distribution J1' including this magnetic field variation C1. On the other hand, magnetic field distribution J2 produced by the ferromagnetic bodies generally indicates the characteristic to be nonlinear with respect to the external magnetic field intensity (mainly the magnetic field produced by the superconductive magnet), and hardly varies in the vicinity of the saturation region. Therefore, magnetic field variation C1 produced by the superconductive coil with respect to homogeneous magnetic field J3 is reflected as it is after the applied current value to the superconductive coil is varied, and homogeneous magnetic field J3 turns to inhomogeneous magnetic field distribution J3'.

Though such variation of magnetic field homogeneity attributed to error in the applied current value can be prevented by exactly matching the applied current value before demagnetization and the applied current value after the re-excitation, the accuracy thereof depends on the accuracy of a power source for excitation. However, highly accurate power source for excitation is quite expensive.

Such fluctuation of magnetic field homogeneity can be corrected by the method for generating homogeneous magnetic field by re-arranging the magnetic field homogeneity adjusting body as disclosed in Patent Document 1, but it takes a long time for adjustment operation as previously mentioned, which is not an adequate method from the perspective of operation time. Also, in the method for generating homogenous magnetic field by controlling temperature distribution of the magnetic body as is disclosed in Patent Documents 5 and 6, it is not effective unless the main magnetic coil is configured by a permanent magnet or some other kinds of magnet as is evidenced by the fact that the superconductive magnet is not listed as a target magnetic material in the Patent Documents. In this method, it is also difficult to generate temperature distribution to compensate a very small inhomogeneity attributed to error in the coil current value, and even if it is possible the configuration thereof will be very complex and expensive. Also, the method disclosed in Patent Documents 2-4 can not be used for compensation of current error in a superconductive coil. In the Patent Document 6, consideration of compensation for current error in the superconductive coil is not addressed.

Given this factor, the objective of the present invention is to provide a superconductive magnet device and a magnetic resonance imaging apparatus capable of acquiring homogeneous magnetic field by compensating inhomogeneous magnetic field attributed to error in excitation current of the superconductive coil effectively and inexpensively.

Means to Solve the Problem

As a result of earnest consideration, the present inventors found out that it is possible to sufficiently compensate fluctuation of magnetic field homogeneity attributed to error in the applied current value of the superconductive coil by changing the temperature of the ferromagnetic body itself, and completed the present invention.

The superconductive magnet and the magnetic resonance imaging apparatus of the present invention are characterized in comprising:

a magnetic field generating device having a superconductive coil and a ferromagnetic body;

a temperature variation calculating device configured to calculate temperature variation of the ferromagnetic body for compensating magnetic field inhomogeneity in a magnetic field space; and a temperature control device configured to control the temperature of the ferromagnetic body based on the temperature variation calculated by the temperature variation calculating device.

Also, the magnetic field inhomogeneity compensation method in the above-mentioned superconductive magnet and the magnetic resonance imaging apparatus of the present invention comprises:

a step to measure magnetic field inhomogeneity in a magnetic field space;

a step to calculate temperature variation of a ferromagnetic body for compensating magnetic field inhomogeneity; and a step to control temperature of a ferromagnetic body itself based on the calculated temperature variation.

By applying the above-described configuration, temperature variation of a ferromagnetic body necessary to improve magnetic field inhomogeneity in a magnetic field space is calculated based on the magnetic field distribution measured by the magnetic field distribution measuring device by the temperature variation calculating device, and the temperature control value of the ferromagnetic body itself is set by the temperature control device based on the calculated temperature variation. In other words, since inhomogeneous magnetic field generated due to an error in an applied current value of a superconductive coil can be compensated using the temperature control device for controlling the temperature of the ferromagnetic body so as to acquire homogeneous magnetic field, it is possible to adjust magnetic field inohomogeneity of a superconductive magnetic device more effectively and inexpensively compared to the conventional methods. Therefore, it is possible to provide a superconductive magnetic device or magnetic resonance imaging apparatus comprising such magnetic field adjusting function capable of effectively adjusting a magnetic field at low cost.

EFFECT OF THE INVENTION

In accordance with the present invention, it is possible to provide a superconductive magnetic device and a magnetic resonance imaging apparatus capable of acquiring magnetic field homogeneity by effectively and inexpensively compensating magnetic field inhomogeneity attributed to an error in an excitation current of a superconductive coil.

BRIEF DESCRIPTION OF THE DIAGRAMS

DESCRIPTION OF THE SYMBOLS

1: superconductive magnetic device, 1A and 1B: coil container, 2A and 3A: superconductive coil, 2B and 3B: superconductive coil, 4A and 5A: iron, 4B and 5B: iron, 8 heat transfer tube, 9: heat transfer tube, 10: electric heater, 12: temperature control device, 20: magnetic field homogeneity adjusting device, 21: magnetic field distribution measuring device, 22: temperature variation calculating device, 26: temperature sensor, 30: analysis means, BD: bed, Bmax and Bmin: magnetic field fluctuation, C1 and C1': magnetic field fluctuation, F: homogeneous magnetic field space, J1 and J1': magnetic field distribution, J2 and J2': magnetic field distribution, J3: homogeneous magnetic field

BEST MODE TO CARRY OUT THE INVENTION

Figure 1:
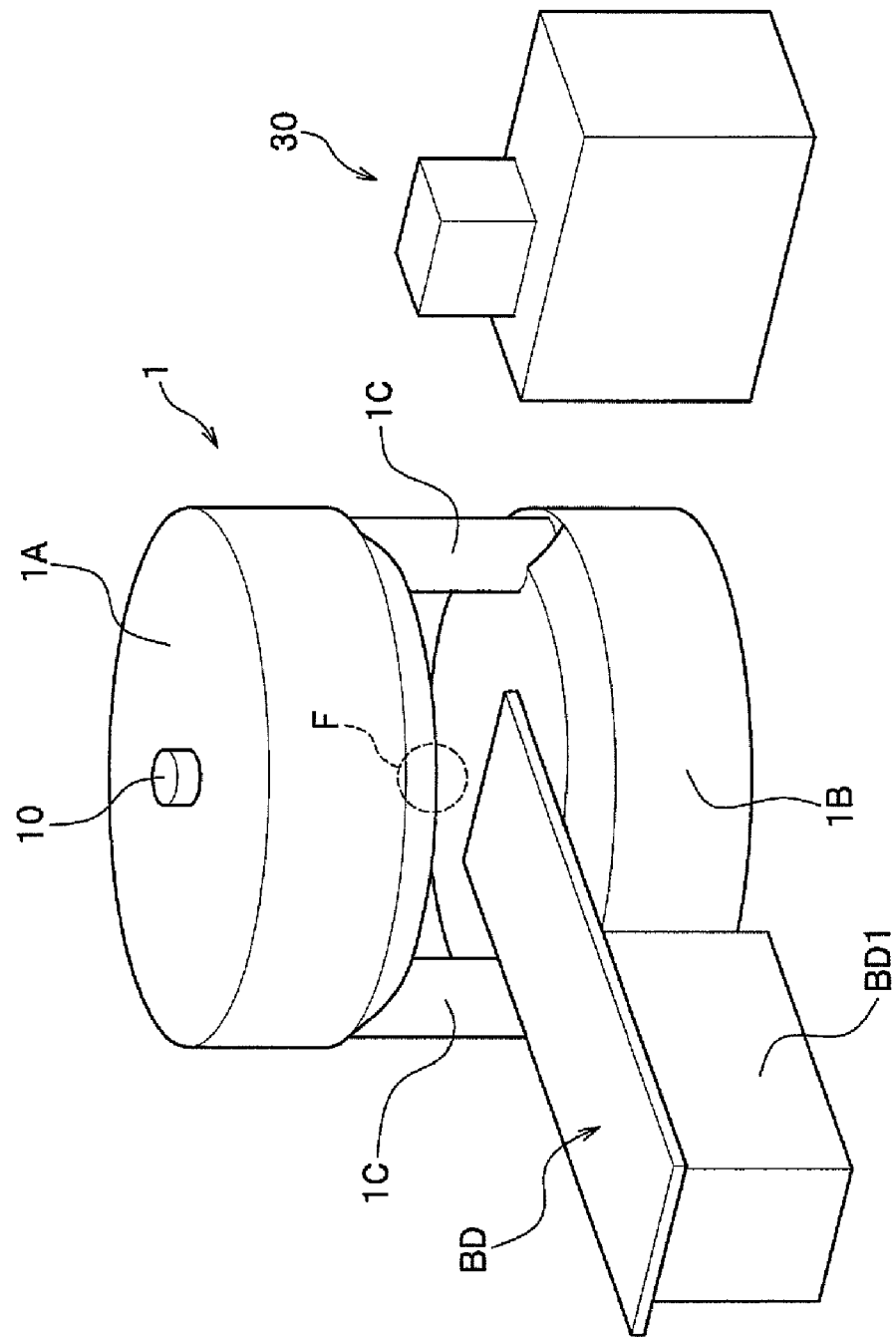
FIG. 1 is an explanatory diagram showing a magnetic resonance imaging apparatus comprising a superconductive magnetic device of the present invention.
Figure 3:
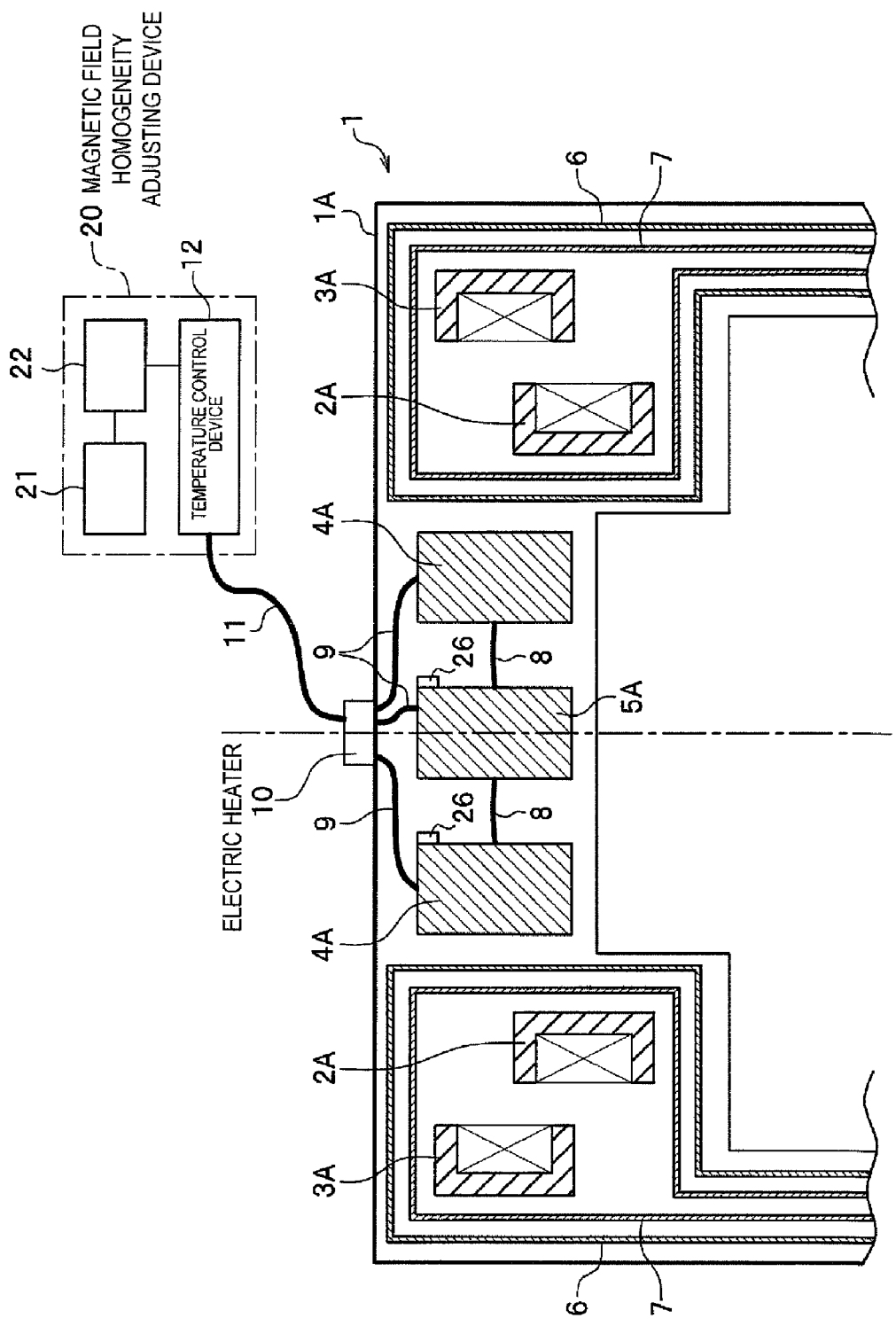
FIG. 3 is a pattern cross-sectional view of the main units of the superconductive magnetic device.

Next, an embodiment of the magnetic resonance imaging apparatus (hereinafter, referred to as an MRI apparatus) using a superconductive magnetic device comprising a magnetic field homogeneity adjusting device of the present invention will be described in detail referring to the attached diagrams. The MRI apparatus is configured, as shown in FIG. 1, by superconductive magnetic device 1, bed BD for placing an object to be examined (not shown in the diagrams, same as below), transfer means BD1 for transferring the object placed on the bed BD to imaging region F in a homogeneous magnetic field, to which a driving mechanism not shown in the diagram is provided and analysis means 30 which is formed by devices such as a computer for analyzing nuclear magnetic resonance signals from the object which is transferred to the imaging region by the transfer means BD1, for the purpose of imaging tomograms through the object placed on the bed BD. To the superconductive magnetic device 1, magnetic field homogeneity adjusting device 20 (refer to FIG. 3 and FIG. 4) which is the characteristic configuration of the present invention is provided.

Figure 2:
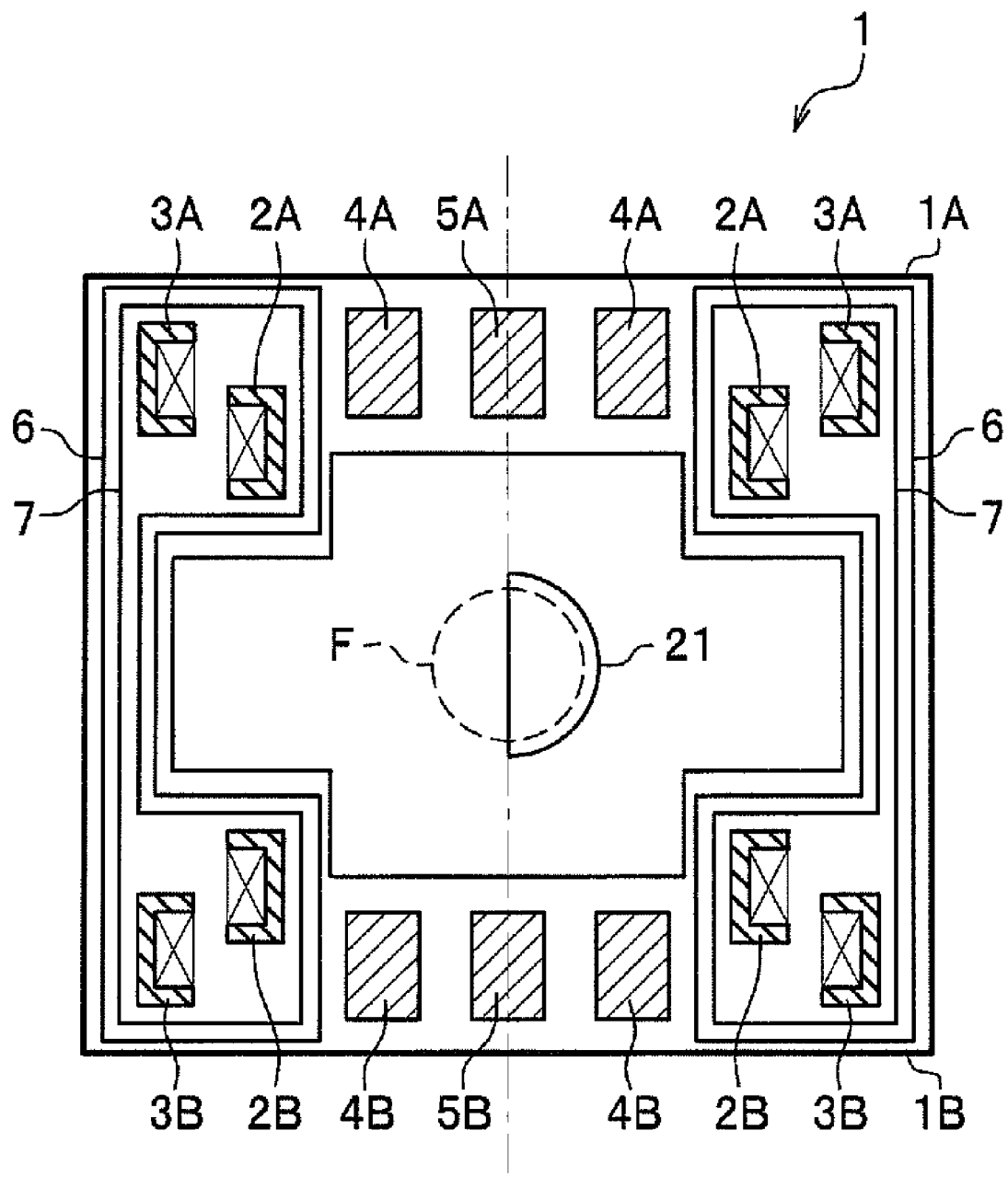
FIG. 2 is a pattern cross-sectional view showing the configuration of the superconductive magnetic device.

The superconductive magnetic device 1 is configured as a magnetic field generation source such that a pair of coil containers 1A and 1B of which the inside is evacuated, form a magnetic field space by being vertically disposed facing each other via connecting poles 1C and 1C. As shown in FIG. 2, annular-formed superconductive coils 2A and 3A are provided to the upper coil container 1A, and as annular-formed or column-shaped iron 4A and 5A as a ferromagnetic body are provided inside of the superconductive coils 2A and 3A radially. To the lower coil container 1B, superconductive coils 23 and 3B to be paired with superconductive coils 2A and 3A of the upper coil container 1A are provided, and iron 4B and 5B as ferromagnetic bodies to be paired with iron 4A and 5B of the upper coil container 1A are further provided. As for the coil wire member of the respective superconductive coils 2A, 3A, 2B and 3B, for example, NbTi wire member is used.

Since upper coil container 1A and lower coil container 1B of the present embodiment have the same configuration, the configuration of only the upper coil container 1A will be described below.

The upper coil container 1A is a tube-like vacuum container (second container), and helium container (first container) 7 is stored therein via radiation shield 6. In helium container 7, superconductive coils 2A and 3A are stored along with liquid helium (not shown in the diagram) as a refrigerant for superconduction. Superconductive coil 2A to be disposed inside of the upper coil container 1A radially is a main coil, and superconductive coil 3A to be disposed outside thereof radially is a shielding coil.

Iron 4A and 5A are disposed in a vacuum region of coil container 1A which is the inside of the helium container 7 radially. A plurality of heat transfer tubes 8 are disposed between iron 4A and A (in other words, the respective iron pieces are thermally connected by the heat transfer tube), and the temperature of iron 4A and 5A is maintained evenly via the heat transfer tube 8. In the present embodiment, a plurality of heat transfer tubes 8 are provided radially in a planar view leaving predetermined intervals therebetween in the circumferential direction of iron 4A and 5A, and the material or dimensions, etc. are appropriately set so that the temperature of iron 4A and 5A are to be the same. As for the material for the heat transfer tube 8, the material which has high thermal conductivity, for example, copper is used. Forming the heat transfer tube 8 by, for example, a mesh material can make it possible to flexibly respond to problems such as vibration of superconductive magnetic device 1.

Electric heater 10 is disposed on the external top surface of the upper coil container 1A, and the intervals between this electric heater 10 and iron 4A and 4A are connected by a plurality of heat transfer tubes 9. Also, the intervals between electric heater 10 and iron 4B and 5B of the lower coil container 10 are connected by heat transfer tube 9 which is not shown in the diagram (disposed through the inside of connecting poles 1C and 1C). Therefore, when heat is generated by electric heater 10 being turned on, the heat is transmitted to iron 4A and 5A (iron 4B and 5B) via heat transfer tube 9, and the temperature of these iron 4A and 5A (iron 4B and 5B) are to be increased. Also, iron 4A and 5A (iron 4B and 5B) are configured so that the temperature is to be maintained evenly by the plurality of heat transfer tubes 8.

Here, "to maintain the temperature evenly" includes to maintain temperature of the entire iron 4A and 5A (iron 4B and 5B) the same, and also includes the case that the temperature of the respective irons are raised by the same level while they have the similar temperature difference from the beginning to a certain extent so as to maintain the temperature variation of iron 4A and 5A (4B and 5B) (the case that magnetic field homogeneity is obtained while iron 4A and 5A (4B and 5B) have the same temperature difference to a certain extent).

Such heat control by electric heater 10 is configured to be performed by temperature control device 12 to be described later which is connected via link line 11.

Since iron 4A and 5A (4B and 5B) are to be heated by electric heater 10 as well as being cooled by radiation to radiation shield 6 disposed on the side of the heater, temperature of iron 4A and 5A (iron 4B and 5B) is determined by the balance between the heating by electric heater 10 and the cooling by radiation shield 6.

Temperature sensor 26 is mounted on iron 4A and 5A so the temperature thereof can be measured. The temperature measured by temperature sensor 26 is transmitted to temperature control device 12 to be described later. It may be set so that a plurality of temperature sensors 26 are disposed to each of iron 4A and iron 5A so as to measure the temperature in the respective disposed positions.

In the present embodiment, it is configured so that one temperature control device 12 controls the temperature of both iron 4A and 5A of the upper coil container 1A and iron 4B and 5B of the lower coil container 1B. In other words, temperature control device 12 is shared by iron 4A and 5A of the upper coil container 1A and iron 4B and 6B of the lower coil container 1B, and in this example, the temperature of iron 4B and 5B of the lower coil container 1B is controlled on the basis of the temperature of iron 4A and 5A of the upper coil container 1A.

Figure 4:
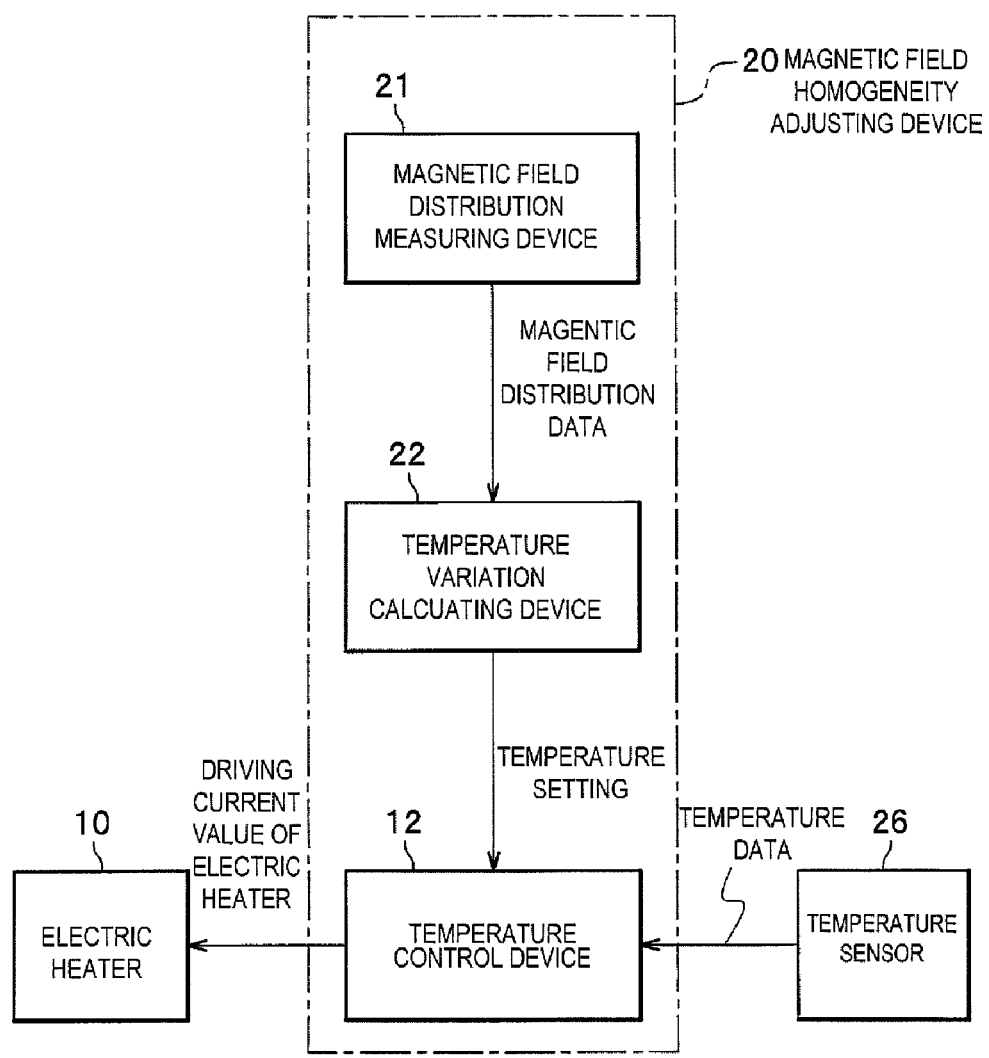
FIG. 4 is a block diagram showing a magnetic field inhomogeneity adjusting device.

Magnetic field homogeneity adjusting device 20 is configured comprising magnetic field distribution measuring device 21, temperature variation calculating device 22 and temperature control device 12 as shown in FIG. 4.

Magnetic field measuring device 21 is for measuring magnetic field distribution in a magnetic field space, and is disposed in the magnetic field space after excitation of superconductive magnetic device 1 (refer to FIG. 2).

Magnetic field distribution measuring device 21 is for measuring magnetic field distribution in homogeneous magnetic field space F (refer to FIG. 2, same as below), for example, it may be configured so that the magnetic sensors not shown in the diagrams are disposed on the respective points on homogeneous magnetic field F point by point for measurement, or that a plurality of magnetic sensors are mounted in a half-circular form for measuring magnetic field intensity of the plural points at the same time. Such configured magnetic field distribution measuring device 21 is to be removed after completing adjustment of magnetic field for acquiring magnetic field homogeneity. It is also sufficient to use the method for measuring magnetic field distribution from magnetic resonance spectra of a water phantom, etc. without performing direct measurement using the above-mentioned magnetic sensors.

The magnetic field distribution data acquired by magnetic field distribution measuring device 21 is inputted to temperature variation calculating device 22.

Temperature variation calculating device 22 calculates temperature variation $\Delta T$ of iron 4A and 5A of the upper coil container 1A and iron 4B and 5B of the lower coil container 1B which is necessary for compensating magnetic field inohomogeneity of a magnetic field space to improve homogeneity, based on the magnetic field distribution data measured by the magnetic field distribution measuring device 21.

Temperature control device 12 sets the temperature control value of iron 4A and 5A (iron 4B and 5B) based on temperature variation $\Delta T$ calculated by temperature variation calculating device 22, and controls the temperature of iron 4A and 5A (iron 4B and 5B) based on the set temperature control value. The temperature data measured by temperature sensor 26 is to be inputted to temperature control device 12.

Next, sufficient compensation of magnetic field inhomogeneity attributed to an error in an applied current value of superconductive coils 2A and 3A by homogeneous temperature variation of iron 4A and 5A (4B and 5B) will be described referring to formulas and FIG. 5.

Figure 5:
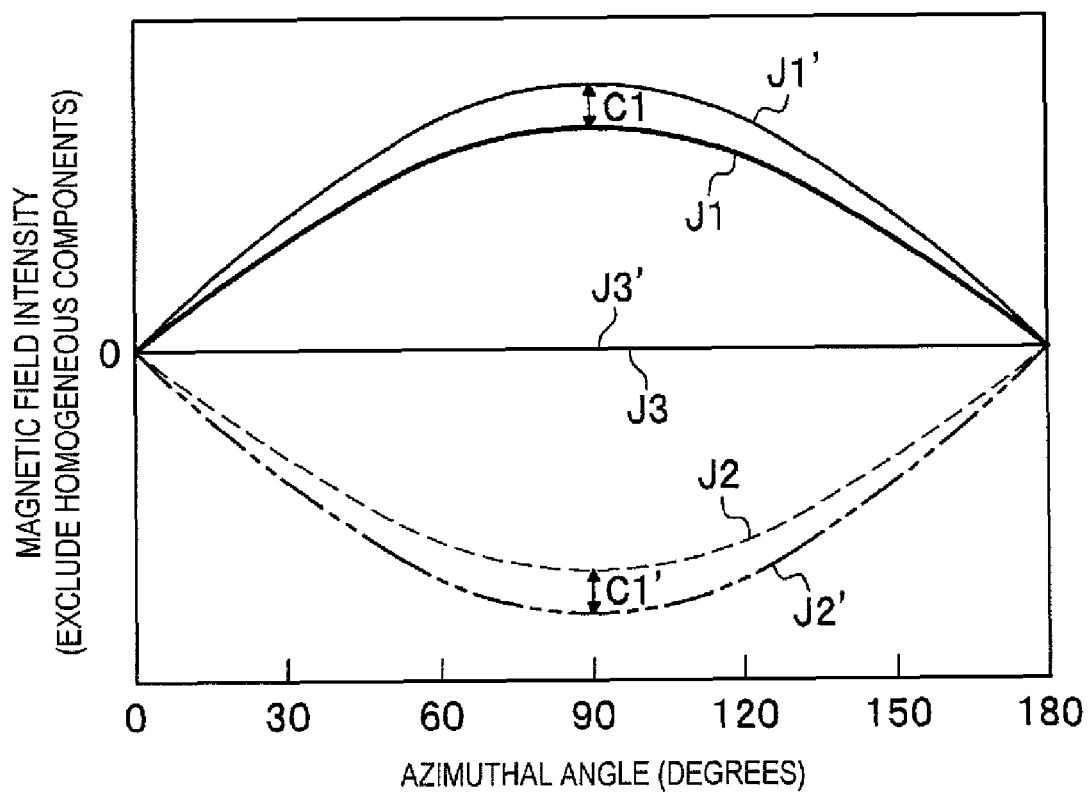
FIG. 5 shows the principle that it is possible to compensate inhomogeneous magnetic field attributed to an error in the current value of the superconductive coil by temperature of iron.

In FIG. 5, the lateral axis indicates an azimuthal angle (degrees) of a homogeneous magnetic field, and the vertical axis indicates the magnetic field intensity (excluding homogeneous components) in the direction thereof. As previously mentioned, homogeneous magnetic field J3 is formed by sum of magnetic field distribution J1 produced by superconductive coils 2A and 3A (2B and 3B) and magnetic field distribution J2 produced by iron 4A and 5A (4B and 5B).

The magnetic field distribution produced by super-conductive coils 2A and 3A (2B and 3B) upon generation of error $\Delta I$ (not shown in the diagram) of the applied current value of superconductive coils 2A and 3A (2B and 3B) turns out to be magnetic field distribution J1', which generates magnetic field change C1 from magnetic field distribution J1 to magnetic field distribution J1'. Since magnetic field distribution J1 and magnetic field distribution J1' are proportional to the applied current value of superconductive coils $2a$ and 3A (2B and 3B), magnetic field change C1 is also proportional to the applied current value of superconductive coils 2A and 3A (2B and 3B). Here, when magnetic field distribution J1 and magnetic field change C1 are respectively expressed using vectors as:

$$\vec{A}$$

$$\vec{B},$$

since the magnetic field distribution produced by super-conductive coils 2A and 3A (2B and 3B) are proportional to the applied current value of superconductive coils 2A and 3A (2B and 3B), it can be expressed by the following formula (1).

$$\vec{B} = \alpha \Delta I \vec{A} \qquad \text{formula (1)}$$

Here, $\alpha$ is a constant of proportion.

On the other hand, iron 4A and 5A (4B and 5B) have temperature dependency that the volume of saturated magnetization decreases along with increase of temperature. This magnetization change can be linearly approximated with respect to temperature variation in the temperature range in the vicinity of normal temperature wherein magnetic resonance imaging apparatuses are generally operated, that is the temperature range smaller compared to the temperature range of iron 4A and 5A (4B and 5B). Therefore, when the temperature of iron 4A and 5A (4B and 5B) which produces magnetic field distribution J2 is evenly raised for $\Delta T$, iron 4A and 5A (4B and 5B) evenly loses magnetization for the portion which is proportional to $\Delta T$, and the magnetic field distribution produced by iron 4A and 5A (4B and 5B) turns out to be magnetic field distribution J2' while generating magnetic field change C1'. Here, when magnetic field distribution J2 and magnetic field change C1' are respectively expressed using a vector as:

$$\vec{C}$$

$$\vec{D},$$

since the magnetic field distribution produced by iron 4A and 5A (4B and 5B) is proportional to the magnetization of iron 4A and 5A (4B and 5B), i.e. proportional to the temperature variation, it can be expressed by the following formula (2).

$$\vec{D} = \beta \Delta T \vec{C} \qquad \text{formula (2)}$$

Here, $\beta$ is a constant of proportion.

Meanwhile, since it is configured that the sum of magnetic field distribution J1 produced by superconductive coils 2A and 3A (2B and 3B) and magnetic field distribution J2 produced by iron 4A and 5A (4B and 5B) forms homogeneous magnetic field J3, magnetic field distribution J1 and magnetic field distribution J2 are the same in the size of magnetic field distribution except homogeneous magnetic field components, while facing the opposite directions. These relationships can be expressed by the following formula (3).

$$\vec{A} = -\vec{C} \qquad \text{formula (3)}$$

By this formula, formula (4) can be obtained using the previous formulas (1), (2) and (3).

$$\vec{D} = -\frac{\beta}{\alpha} \frac{\Delta T}{\Delta I} \vec{B} \qquad \text{formula (4)}$$

This formula (4) indicates that, by selecting appropriate temperature variation ΔT, it is possible to make magnetic field change C1 attributed to an error in the applied current value of a coil and magnetic field change C1' generated due to temperature variation of iron 4A and 5A (4B and 5B) to have the same size of distribution while facing the opposite directions to each other. In other words, it indicates that it is possible to eliminate magnetic field C1 attributed to ΔI using magnetic field C1' generated by ΔT, and to obtain magnetic field distribution J3'.

While the calculation of the formula can be performed using formula (4) as it is, the calculation thereof can be made simpler by devising the expression of magnetic field change C1 or magnetic field C1'. For example, by using Bu which is calculated from Bmax which is the maximum magnetic field change out of magnetic field change C1 and Bmin which is the minimum magnetic field change thereof as shown in the following formula (5), temperature variation ΔT can be expressed as the following formula (6) using constant of proportion γ:

$$B_u = B_{max} - B_{min} \quad \text{formula (5)}$$

$$\Delta T = \gamma B_u \quad \text{formula (6).}$$

Also, expansion coefficient of orthogonal expansion can be used. In the case that magnetic field change C1 is expressed not by a vector form but by a function using a polar coordinate as:

$$C(\theta, \phi),$$

the orthogonal expansion such as the following formula (7) can be expressed as an example.

$$C(\theta, \phi) = \sum_{l,m} (A(l,m)\cos(m\phi) + B(l,m)\sin(m\phi)) P_l^m(\cos\theta) \quad \text{formula (7)}$$

In this regard, however, $$P_l^m(\cos\theta)$$

is an associated Legendre function. When magnetic field change C1 is expressed by such coefficients A(l,m) and B(l,m) of orthogonal expansion, since magnetic field variation C1 changes for the portion which is proportional to the applied current value of superconductive coils 2A and 3A (2B and 3B), by referring to one expansion coefficient all of the remaining expansion coefficients can be determined. Therefore, for example, by referring to the expansion coefficient expressed by A(2,0), ΔT can be calculated as expressed in the following formula (8) using ratio coefficient γ' (variations of temperature and magnetic field are in proportion to each other, i.e. on the premise of formula (4)).

$$\Delta T = \gamma' A(2,0) \quad \text{formula (8)}$$

While formulas (4), (6) and (8) are exemplified as calculation method of ΔT in the present embodiment, temperature variation calculating device 22 may use any method for calculating appropriate temperature variation ΔT from the measured magnetic field change 1. The calculated ΔT is to be inputted to temperature control device 12 as data.

Temperature control device 12 receives ΔT which is calculated in temperature variation calculating device 22 and the temperature data measured by temperature sensor 26 being disposed in iron 4A and 5A as inputted information, determines and outputs the drive current value of electric heater 10 which is necessary for changing the temperature of iron 4A and 5A for the portion of ΔT. As for the method for determining the drive current value, for example, well-known control methods such as proportional control, integral control, differential control or the combination thereof can be used. Or without limiting to those methods, sensor-less control which does not require temperature sensor 26 may be used.

Hereinafter, the effect to be acquired by the present embodiment will be described.

(1) Magnetic field homogeneity adjusting device 20 of the present embodiment comprises magnetic field distribution measuring device 21 for measuring magnetic field distribution, temperature variation calculating device 22 for calculating necessary temperature variation ΔT from the magnetic field distribution obtained by magnetic field distribution measuring device 21 and temperature control device 12 for controlling the temperature of iron 4A and 5A (4B and 5B) based on temperature variation ΔT calculated by temperature variation calculating device 22, thus iron 4A and 5A (4B and 5B) can be controlled to have appropriate temperature for corresponding to magnetic field variation C1 and magnetic field homogeneity adjustment can be performed effectively even in the case that an error is generated in an applied current value of superconductive coils 2A and 3A (2B and 3B). Also, since the temperature of iron 4A and 5A (4B and 5B) does not have to have distribution, it is possible to have a configuration having the minimum number of devices such as electric heater 10 or temperature control device 12, and to acquire a simple and inexpensive magnetic field homogeneity adjusting device 20.

(2) By configuring temperature variation calculating device 22 to calculate temperature variation ΔT as the amount which is proportional to the difference between the maximum value and the minimum value of the measured magnetic field distribution, calculations can be made simple and a simple and inexpensive magnetic field homogeneity adjusting device 20 can be provided.

(3) When it is configured that temperature variation ΔT to be calculated as the amount which is in proportion to the size of the coefficient of orthogonal expansion of the magnetic field distribution, since magnetic field variation C1 changes only for the portion which is in proportion to the applied current value of superconductive coils 2A and 3A (2B and 3B), by referring to one expansion coefficient all of the remaining coefficients can be determined which makes it possible to make the calculation simple and to provide a simple and inexpensive magnetic field homogeneity adjusting device 20.

(4) Since temperature control device 12 is configured to compensating inhomogeneous magnetic field generated due to an error in the applied current value of superconductive coils 2A and 3A (2B and 3B) by a simple temperature control merely generating even temperature distribution of iron 4A and 5A (4B and 5B) (i.e. not necessary to give temperature distribution to iron 4A and 5A (4B and 5B)) for acquiring homogeneous magnetic field, magnetic field homogeneity adjusting device 20 of superconductive magnetic device 1 can be provided with more effective and less expensive configuration.

(5) Since temperature control device 12 is shared by iron 4a and 5A and iron 4B and 5B, magnetic field homogeneity adjusting device 20 can be simple and inexpensive.

(6) Since electric heater 10 is disposed on the external top surface of the upper coil container 1A, replacement thereof due to inspection or maintenance can be performed easily which makes maintenance performance of the device superior.

(7) Since magnetic field homogeneity adjusting device 20 of the present embodiment is simple and inexpensive, it is possible to provide superconductive magnetic device 1 or a magnetic resonance imaging apparatus comprising this magnetic field homogeneity adjusting device 20 for adjusting magnetic field effectively.

Figure 6:
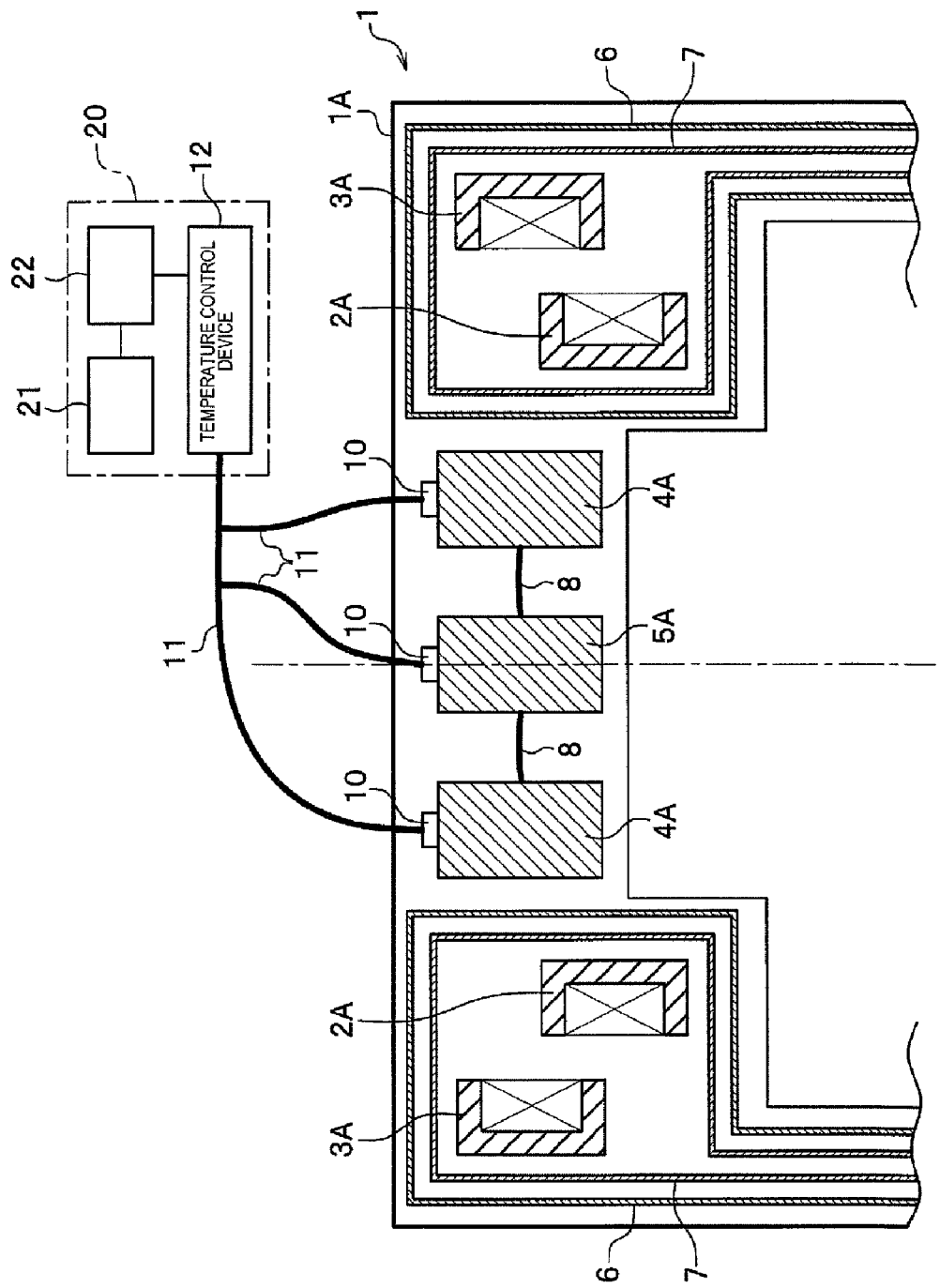
FIG. 6 is a pattern cross-sectional view showing a variation example of the superconductive magnetic device.

FIG. 6 is a variation example of superconductive magnetic device 1, and electric heater 10 is directly disposed to iron 4A and 5A (4B and 5B, not shown in the diagram, same as below) in this example. By such configuration, iron 4A and 5A (4B and 5B) can be directly heated by electric heater 10, and thermal loss and necessary heating value of electric heater 10 can be reduced. Electric heater 10 may be directly disposed at least to one iron.

Figure 7:
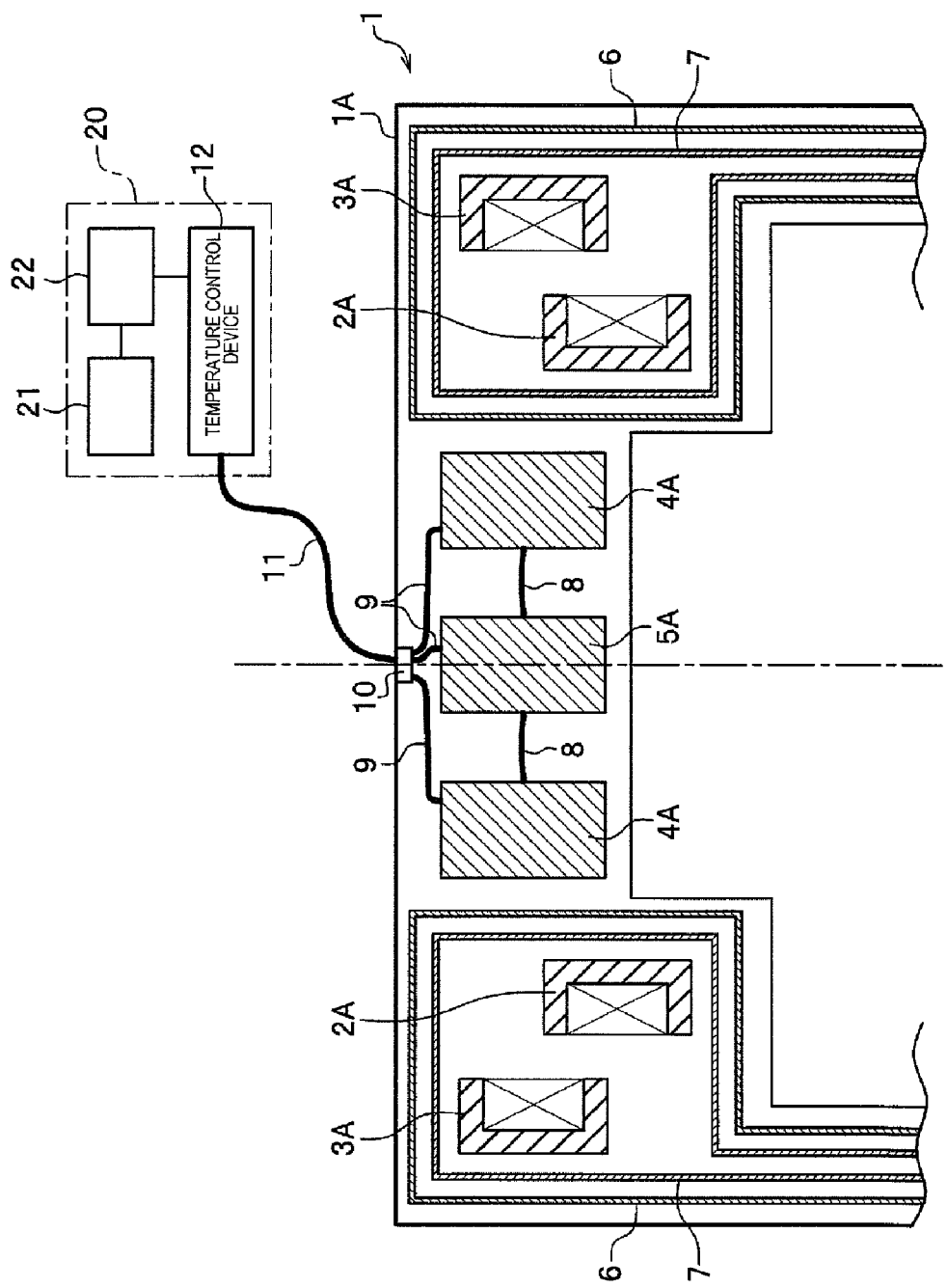
FIG. 7 is a pattern cross-sectional view showing a variation example of the superconductive magnetic device.

FIG. 7 is another variation example of superconductive magnetic device 1, and electric heater 10 is disposed inside of the upper coil container 1A in this example. The inside of coil container 1A is evacuated and insulated, and by disposing electric heater 10 inside of coil container 1A the heat of electric heater 10 can escape easily. The necessary heating value in electric heater 10 can be reduced by that much.

Figure 8:
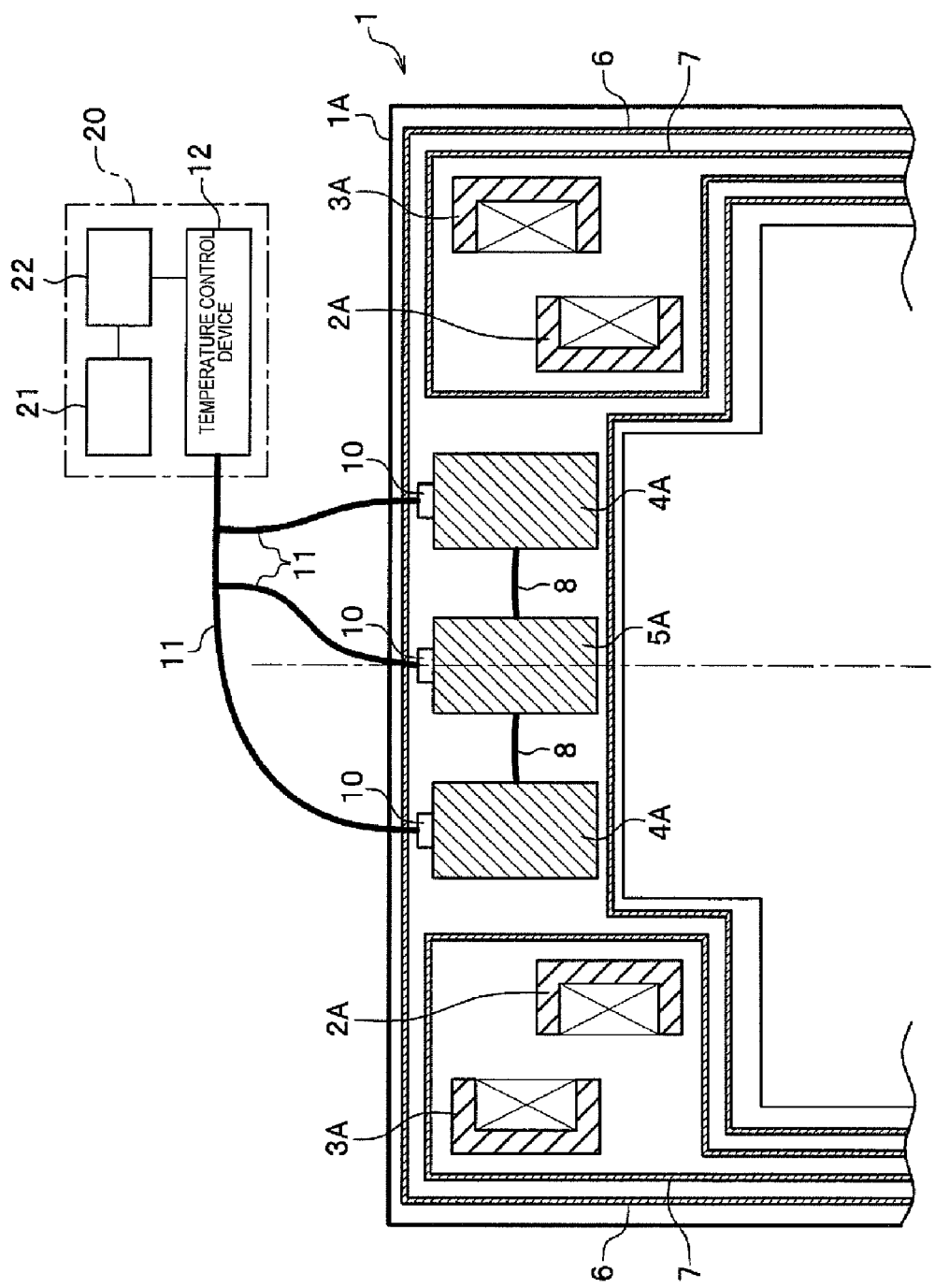
FIG. 8 is a pattern cross-sectional view showing a variation example of the superconductive magnetic device.
Figure 9:
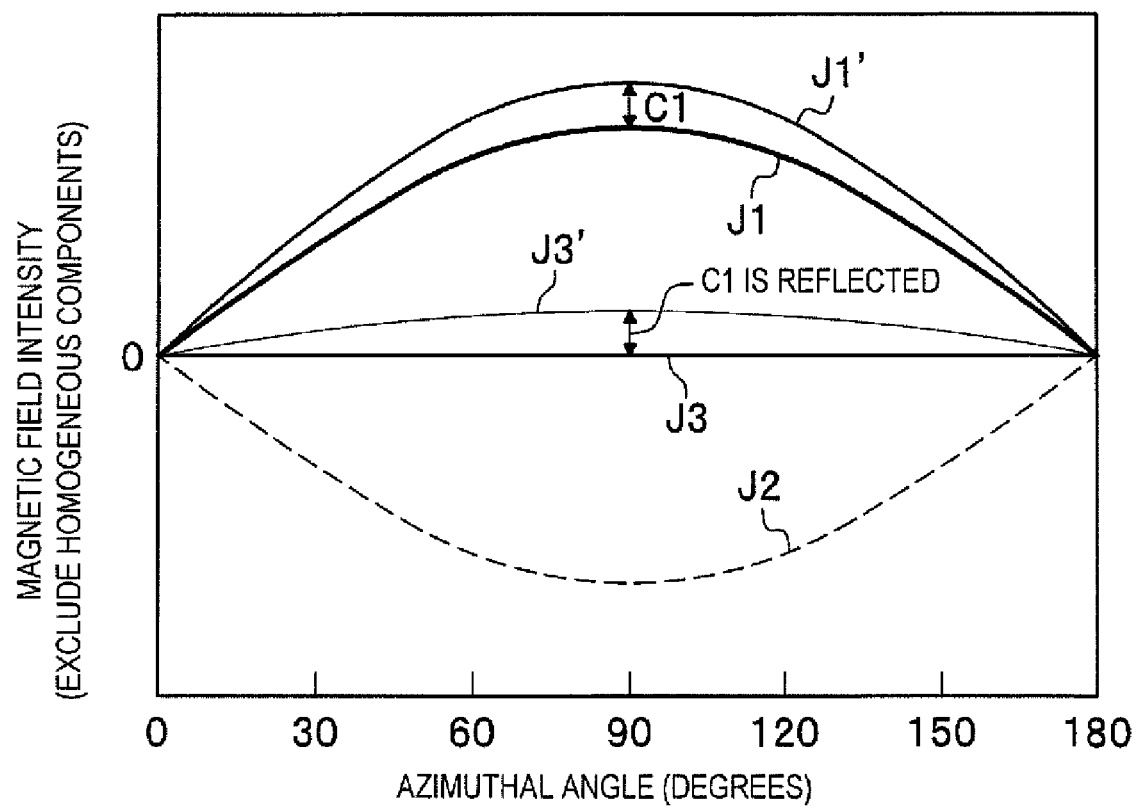
FIG. 9 shows the principle that magnetic field inhomogeneity fluctuates when an error is generated in the applied current value of a superconductive coil.

FIG. 8 is another variation example of superconductive magnet device 1. In this example, iron 4A and 5A (4B and 5B) are disposed inside of radiation shield 6, and electric heater 10 is disposed directly to iron 4A and 5A (4B and 5B). Though by such configuration the temperature of iron 4A and 5A (4B and 5B) is lowered in the proximity of the temperature of radiation shield 6, by configuring the device capable of varying temperature variation ΔT by temperature variation control device 12, it is possible to accomplish uniform temperature distribution in iron 4A and 5A (4B and 5B).

Iron 4A and 5A (4B and 5B) or electric heater 10 may be disposed in any appropriate positions without being limited to the examples above.

Also while the upper coil container 1A and the lower coil container 1B shared temperature control device 12 in the above-described embodiment, it may be configured so that temperature control devices are disposed to the upper coil container 1A and the lower coil container 1B respectively. Depending on the environment for setting superconductive magnetic device 1, the temperature near the upper coil container 1A and the temperature near the lower coil container 1B are different and the temperature may vary as time advances. Such influence can be eliminated by disposing temperature control device 12 individually which contributes to the high accuracy of magnetic field homogeneity. Electric heater 10 which corresponds to the lower coil container 1B (not shown in the diagram) may be disposed using the outer external side surface, etc. of the lower coil container 1B, or storing in the space prepared in the lower part of the lower coil container 1B of electric heater 10.

The invention claimed is:

1. A superconductive magnetic device comprising:
a magnetic field generating device configured having a superconductive coil and a ferromagnetic body;
a temperature variation calculating device configured to calculate temperature variation of the ferromagnetic body for compensating magnetic field inhomogeneity in a magnetic field space;
a temperature control device configured to control the temperature of the ferromagnetic body based on the temperature variation calculated by the temperature variation calculating device; and
a plurality of the ferromagnetic bodies, wherein the plurality of ferromagnetic bodies are connected to each other by heat transfer members, and the plurality of heat transfer members are disposed radially in a planar view leaving predetermined intervals therebetween in the circumferential direction of the ferromagnetic body.

2. The superconductive magnetic device according to claim 1, wherein the ferromagnetic field body is disposed inside of the superconductive coil.

3. The superconductive magnetic device according to claim 2, wherein:
the superconductive coil is formed in a toric shape, and has a first container for containing the superconductive coil and a second container which is evacuated therein for containing the first container; and
the ferromagnetic body is disposed inside of the first container in the diameter direction and in the intrinsic range of the second container.

4. The superconductive magnetic device according to claim 3, characterized in that a radiation shield is disposed between the first container and the second container.

5. The superconductive magnetic device according to claim 4, wherein the ferromagnetic body is disposed inside of the radiation shield.

6. The superconductive magnetic device according to claim 3, wherein the first container is formed in a tonic shape.

7. A magnetic resonance imaging apparatus comprising the superconductive magnetic device according to claim 1.

8. The superconductive magnetic device according to claim 1, characterized in that at least one temperature sensor is disposed in the ferromagnetic body, wherein the temperature control device receives the input of temperature information of the ferromagnetic body which is measured by the temperature sensor and controls the temperature of the ferromagnetic body based on the inputted temperature information.

9. The superconductive magnetic device according to claim 1, comprising a heater for providing heat to the ferromagnetic body via the heat transfer member, wherein the temperature control device controls the heat generation of the heater.

10. The superconductive magnetic device according to claim 9, wherein the heater is directly disposed inside of at least one of the plurality of ferromagnetic bodies.

11. The superconductive magnetic device according to claim 9, wherein the magnetic field generating device further comprises one or more pole pieces, and the one heater is disposed to adjust temperature distribution of the pole pieces.

12. The superconductive magnetic device according to claim 1, wherein the temperature control device maintains uniform temperature of the ferromagnetic body.

13. The superconductive magnetic device according to claim 1, wherein the temperature control device maintains uniform temperature variation of the plurality of ferromagnetic bodies.

14. A superconductive magnetic device comprising:
a magnetic field generating device configured having a superconductive coil and a ferromagnetic body;
a temperature variation calculating device configured to calculate temperature variation of the ferromagnetic body for compensating magnetic field inhomogeneity in a magnetic field space; and
a temperature control device configured to control the temperature of the ferromagnetic body based on the temperature variation calculated by the temperature variation calculating device,
wherein the temperature variation calculating device calculates the temperature variation as the amount which is proportional to the difference between the maximum value and the minimum value of the measured magnetic field distribution.

15. A superconductive magnetic device comprising:
a magnetic field generating device configured having a superconductive coil and a ferromagnetic body;
a temperature variation calculating device configured to calculate temperature variation of the ferromagnetic body for compensating magnetic field inhomogeneity in a magnetic field space; and
a temperature control device configured to control the temperature of the ferromagnetic body based on the temperature variation calculated by the temperature variation calculating device,
wherein the temperature variation calculating device calculates the temperature variation as the amount which is proportional to the size of the coefficient of orthogonal expansion of the magnetic field distribution.

16. A magnetic field inhomogeneity compensation method for compensating magnetic field inhomogeneity in a magnetic field space of the superconductive magnetic device as claimed in claim 1, the method comprising:
a step of measuring magnetic field inhomogeneity of the magnetic field space of the superconductive magnetic device;
a step of calculating temperature variation of the ferromagnetic body for compensating the magnetic field inhomogeneity; and
a step of controlling temperature of the ferromagnetic body based on the calculated temperature variation.

* * * * *